(12) United States Patent
Suh et al.

(10) Patent No.: US 9,498,516 B2
(45) Date of Patent: Nov. 22, 2016

(54) COMPOSITION FOR PREVENTING OR TREATING ERECTILE DYSFUNCTION COMPRISING ANGIOPOIETIN-4 PROTEIN

(71) Applicant: INHA INDUSTRY PARTNERSHIP INSTITUTE, Incheon (KR)

(72) Inventors: Jun Kyu Suh, Seoul (KR); Ji Kan Ryu, Incheon (KR); Mi Hye Kwon, Incheon (KR); Gou Young Koh, Daejeon (KR)

(73) Assignee: INHA INDUSTRY PARTNERSHIP INSTITUTE, Incheon (KR)

( * ) Notice: Subject to any disclaimer, the term of this patent is extended or adjusted under 35 U.S.C. 154(b) by 68 days.

(21) Appl. No.: 14/078,580

(22) Filed: Nov. 13, 2013

(65) Prior Publication Data

US 2014/0148385 A1     May 29, 2014

(30) Foreign Application Priority Data

Nov. 23, 2012  (KR) .................. 10-2012-0133882

(51) Int. Cl.
*A61K 38/00* (2006.01)
*C07K 7/14* (2006.01)
*A61K 38/18* (2006.01)

(52) U.S. Cl.
CPC ............. *A61K 38/1891* (2013.01); *C07K 7/14* (2013.01)

(58) Field of Classification Search
None
See application file for complete search history.

(56) References Cited

U.S. PATENT DOCUMENTS

2007/0298996 A1* 12/2007 Koh et al. ................... 514/2

OTHER PUBLICATIONS

Valenzuela DM et al., Angiopoietins 3 and 4: Diverging gene counterparts in mice and humans, Proc Natl Acad Sci U.S.A., 96(5), pp. 1904-1409, 1999.
Lee HJ et al., Biological characterization of angiopoietin-3 and angiopoietin-4, FASEB J, 18(11), pp. 1200-1208, 2004.

* cited by examiner

*Primary Examiner* — Elizabeth C Kemmerer
*Assistant Examiner* — Regina M Deberry
(74) *Attorney, Agent, or Firm* — The PL Law Group, PLLC (57) ABSTRACT

Provided is a composition for preventing or treating erectile dysfunction including angiopoietin-4 protein as an active ingredient. Angiopoietin-4 protein increases an endothelial cell-specific protein level to induce regeneration of penile vascular endothelial cells, thereby increasing intracavernous pressure. Thus, angiopoietin-4 protein may be efficiently applied to prevention or treatment of erectile dysfunction.

4 Claims, 7 Drawing Sheets

COMPOSITION FOR PREVENTING OR TREATING ERECTILE DYSFUNCTION COMPRISING ANGIOPOIETIN-4 PROTEIN

RELATED APPLICATION

This application claims the benefit of Korean Patent Application No. 10-2012-0133882, filed on Nov. 23, 2012, in the Korean Intellectual Property Office, the disclosures of which are incorporated herein in their entirety by reference.

BACKGROUND

1. Field

One or more embodiments of the present invention relate to a composition for preventing or treating erectile dysfunction including angiopoietin-4 protein as an active ingredient.

2. Description of the Related Art

Erectile dysfunction is a male sexual dysfunction characterized by inability to achieve or maintain an erection sufficient for satisfactory sexual activity. Causes of erection dysfunction are classified into psychogenic and organic causes. Psychogenic erectile dysfunction is caused by an overaction of the sympathetic nervous system due to psychological and emotional impact such as hypersecretion of noradrenaline, increase in tone of corpus cavernosum smooth muscle, and suppression of neurotransmitter secretion. Organic erectile dysfunction is classified into neurogenic erectile dysfunction, vasculogenic erectile dysfunction, and endocrine erectile dysfunction according to the cause thereof.

The vasculogenic erectile dysfunction is caused by damage to penile vascular endothelial cells due to hyperlipidemia, diabetes, hypertension, smoking, cardiovascular diseases, and the like. The vascular erectile dysfunction exhibits insufficient secretion of relaxation neurotransmitters such as nitric oxide (NO) in vascular endothelial cells.

Recently, more research on the organic causes has been conducted, and phosphodiesterase-5 (PDE-5) inhibitors for oral administration such as Viagra (sildenafil citrate) have been generally used to treat erectile dysfunction worldwide. Such medications for oral administration are effective for the treatment of erectile dysfunction via induction of erection by increasing blood flow to the corpus cavernosum. The blood flow is increased since the PDE-5 inhibitor that is specifically distributed in the corpus cavernosum increases a concentration of cGMP. However, side effects, such as headache, facial flushing, indigestion, and heart attack, have been reported, and PDE-5 inhibitor-based drugs such as Viagra cannot be fundamental treatment for erectile dysfunction since they temporarily control molecular level mechanism of expression of proteins and related factors thereof. Moreover, such medications are not highly effective for the treatment of diabetes-induced erectile dysfunction, and the therapeutic effect cannot last for a long period of time.

Thus, there is a need to develop a therapeutic agent for treating erectile dysfunction which fundamentally treating an abnormal vascular structure of the penis and has long-lasting effect.

Meanwhile, angiopoietin-4 protein that is a protein belonging to the angiopoietin family has a coiled-coil domain and a fibrinogen-like domain which are structurally similar to each other. Human angiopoietin-4 protein and mouse angiopoietin-3 are orthologs sharing 65% overall amino acid sequence identity (Valenzuela D M et al., Proc Natl Acad Sci U.S.A., 96(5), pp 1904-9, 1999). Similarly to other angiopoietins, it is known that angiopoietin-4 protein mainly binds to Tie-2 receptor tyrosine kinase, and there has been reported that angiopoietin-4 protein transmits a signal by phosphorylating a Tie-2 receptor in the same manner as angiopoietin-1 (Lee H J et al., FASEB J, 18(11), pp 1200-8, 2004). In addition, there has been reported that angiopoietin-4 protein induces angiogenesis in mouse cornea by activating the Tie-2 receptor (Lee H J et al., FASEB J, 18(11), pp 1200-8, 2004). However, effect of angiopoietin-4 protein on the prevention or treatment of erectile dysfunction has not been reported, and research thereon has not been carried out.

Accordingly, the present inventors conducted research on a composition for preventing or treating erectile dysfunction and discovered that angiopoietin-4 protein has an effect on the treatment for erectile dysfunction since angiopoietin-4 protein increases intracavernous pressure via induction of regeneration of penile vascular endothelial cells by increasing an endothelial cell-specific protein level.

SUMMARY

One or more embodiments of the present invention include a pharmaceutical composition for preventing or treating erectile dysfunction including angiopoietin-4 protein as an active ingredient.

One or more embodiments of the present invention include a food composition for preventing or treating erectile dysfunction including angiopoietin-4 protein as an active ingredient.

One or more embodiments of the present invention include a method of preventing or treating erectile dysfunction of an individual including administrating a pharmaceutical composition for preventing or treating erectile dysfunction into an individual, the pharmaceutical composition including angiopoietin-4 protein or an angiopoietin-4 protein-encoding polynucleotide as an active ingredient.

Additional aspects will be set forth in part in the description which follows and, in part, will be apparent from the description, or may be learned by practice of the presented embodiments.

According to one or more embodiments of the present invention, a pharmaceutical composition for preventing or treating erectile dysfunction includes angiopoietin-4 protein as an active ingredient.

According to one or more embodiments of the present invention, a food composition for preventing or treating erectile dysfunction includes angiopoietin-4 protein as an active ingredient.

According to one or more embodiments of the present invention, a method of preventing or treating erectile dysfunction of an individual includes administrating a pharmaceutical composition for preventing or treating erectile dysfunction into an individual, the pharmaceutical composition including angiopoietin-4 protein or an angiopoietin-4 protein-encoding polynucleotide as an active ingredient.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, a composition for preventing or treating erectile dysfunction includes angiopoietin-4 protein as an active ingredient.

The composition includes a pharmaceutical composition or a food composition.

Hereinafter, the present invention will be described in detail.

In the composition according to the present invention, angiopoietin-4 protein that is an active ingredient includes not only full length angiopoietin-4 protein, but also physiologically active fragments thereof. The physiologically active fragments may substantially have vascular endothelial cell-regenerative activity of angiopoietin-4 protein or genes encoding angiopoietin-4 protein. The physiologically active fragments may have an active domain involved in vascular endothelial cell activity of natural angiopoietin-4 protein. The angiopoietin-4 protein may also include fusion protein of angiopoietin-4 protein in addition to the full length angiopoietin-4 protein or physiologically active fragments thereof. The fusion protein may substantially have vascular endothelial cell-regenerative activity of angiopoietin-4 protein or genes encoding angiopoietin-4 protein. The fusion protein is a protein in which angiopoietin-4 protein or a fragment thereof is linked to a fusion partner that is efficient for separation of angiopoietin-4 protein or the fragment thereof, a fusion partner that is efficient for transmission to a target region, and a fusion partner for improving stability in a living organism, or the like. The partners may be linked to an N-terminal or C-terminal or a side chain of the angiopoietin-4 protein or the fragment thereof. The linking structure may be formed via a covalent or non-covalent bond. The fusion partners may include polypeptides. The fusion partner that is efficient for separation of angiopoietin-4 protein or the fragment thereof may have His sequence, e.g., $His_6$ sequence. The fusion partner that is efficient for transmission to a target region or the fusion partner for improving stability in a living body may have a constant region of an antibody, for example, a common fragment (Fc) region, or may be a polymer, such as polyethylene glycol (PEG), providing resistance against degradation in a living body.

An angiopoietin-4 protein-encoding polynucleotide may be used alone or in a fused form with other substances. For example, the other substances may include at least one selected from the group consisting of a substance capable of transmitting the angiopoietin-4 protein-encoding polynucleotide into a cell, a substance capable of expressing the angiopoietin-4 protein-encoding polynucleotide in a cell via gene expression mechanism, and a substance capable of stably maintaining the angiopoietin-4 protein-encoding polynucleotide within or outside a cell. The fusion may be formed via a covalent or non-covalent bond. The fusion includes a form captured within endoplasmic reticulum.

The angiopoietin-4 protein-encoding polynucleotide may be operationally linked to a gene expression regulatory factor such as a promoter, an operator, an enhancer, and/or a transcription termination factor. The angiopoietin-4 protein-encoding polynucleotide may be inserted into plasmid or viral genome and expressed in a cell. The angiopoietin-4 protein-encoding polynucleotide may have a structure linked to a regulatory factor that regulates specific expression in a penile endothelial cell, for example, a corpus cavernosum endothelial cell or a penile vascular endothelial cell. For example, the angiopoietin-4 protein-encoding polynucleotide may be inserted into adenovirus genome and have a structure linked to a regulatory factor that controls specific expression in a corpus cavernosum endothelial cell or a penile vascular endothelial cell. The structure may be trapped within a virus particle.

Angiopoietin-4 protein according to the present invention induces regeneration of corpus cavernosum endothelial cells or penile vascular endothelial cells in a diabetic erectile dysfunction animal model and increases expressions of platelet/endothelial cell adhesion molecule-1 (PECAM-1) and p-eNOS, which is a vascular endothelial cell-specific protein, in endothelial cells, thereby increasing intracavernous pressure. Thus, angiopoietin-4 protein is effective for improving erectility.

As described above, due to excellent therapeutic effect of angiopoietin-4 protein according to the present invention on erectile dysfunction, angiopoietin-4 protein may be applied to pharmaceuticals and functional foods for preventing or treating erectile dysfunction.

Erectile dysfunction may be caused by malfunction of or damage to penile endothelial cells. Such malfunction of or damage to penile endothelial cells may be caused by hyperlipidemia (including hypercholesterolemic erectile dysfunction), diabetes, hypertension, damage to penile nerves, and any combination thereof, without being limited thereto.

The composition according to the present invention may further include at least one known active ingredient effective for the prevention or treatment of erectile dysfunction in addition to angiopoietin-4 protein.

The composition according to the present invention may further include suitable carriers, excipients, and diluents which are commonly used in preparation of pharmaceutical compositions. The composition may be formulated in any oral formulations such as powders, granules, tablets, capsules, suspensions, emulsions, syrups, and aerosols, formulations for external use, suppositories, or sterilized injection solutions. Formulations disclosed in Remington's Pharmaceutical Science, recent edition, Mack Publishing Company, Easton Pa. may also be used herein. Examples of carriers, excipients, and diluents which may be contained in the composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methylhydroxy benzoate, propylhydroxy benzoate, talc, magnesium stearate, and mineral oil. The composition may be formulated using a filler, an extender, a binder, a wetting agent, a disintegrant, a diluent such as a surfactant, or an excipient. Solid formulations for oral administration may include tablets, pills, powders, granules, and capsules. Such solid formulations may contain one or more excipients such as starch, calcium carbonate, sucrose, lactose, gelatin, and the like. In addition to simple excipients, a lubricant such as magnesium stearate and talc may also be used. Liquid formulations for oral administration may include suspensions, elixirs, emulsions, and syrups. The liquid formulations may further include various excipients, such as, wetting agents, sweeteners, flavors, preservatives, and the like, in addition to simple diluents commonly used in the art such as water and liquid paraffin. Formulations for non-oral administration include sterilized aqueous solutions, non-liquid solutions, suspensions, emulsions, freeze-dried formulations, and suppositories. The non-liquid solutions and suspensions may include propylene glycol, polyethylene glycol, vegetable oils such as olive oil, injectable esters such as ethyloleate, and the like. Bases for the suppositories may include Witepsol, Macrogol, Tween 61, cacao butter, laurin fat, glycerogelatin, and the like.

The term "administration" used herein refers to providing the composition according to the present invention to an individual using any suitable method.

A desirable dose of the pharmaceutical composition according to the present invention may vary according to the condition and weight of a patient, severity of disease, drug form, route and period of administration, and may be chosen by those skilled in the art. An effective daily dose of the composition according the present invention may be in the range of 0.0001 mg/kg to 10000 mg/kg. The composition may be administered once a day or several times a day in divided doses.

The pharmaceutical composition according to the present invention may be administered into individuals via various routes. For example, the pharmaceutical composition may be administered via any expected route such as oral administration, rectal administration, intravenous injection, intramuscular injection, subcutaneous injection, and intracavernous injection.

The composition according to the present invention may be used for the prevention or treatment of erectile dysfunction alone or in combination with surgery, radiation therapy, hormone therapy, chemotherapy, and methods using a biological response modifier.

Used here, the term "functional food" refers to food with regulatory functions in living organisms such as disease prevention and symptom relief, immunity, recovery from illness, and anti-aging. A long-term use of functional foods should not be harmful to human bodies.

Angiopoietin-4 protein according to an embodiment of the present invention may be added to functional foods for the prevention and treatment of erectile dysfunction. The angiopoietin-4 protein may be used added to functional foods alone or in any combination with other foods or ingredients of other foods, as an additive, in an appropriate method common used in the art. Amounts of active ingredients may be determined according to purposes thereof, for example, prevention, health, or treatment. Generally, angiopoietin-4 protein according to the present invention may be added to foods or beverages in an amount of 15% by weight or less, for example, 10% by weight or less, based on the total weight of ingredients. Even though the amounts of the active ingredients in health supplements may be less than the range described above for a long-term use, the amounts may also be increased since the active ingredients are safe.

The type of food is not particularly limited. Examples of food including the active ingredients may be meats, sausages, breads, chocolates, candies, snacks, pizzas, instant noodles and other noodles, gums, dairy products such as ice creams, soups, beverages, teas, drinks, alcohols, vitamins, and other functional foods in common sense.

A composition for functional beverages according to the present invention may further include a variety of flavors, natural carbohydrates, or the like, as additional ingredients in the same manner as other beverages. The natural carbohydrates may include natural sweeteners such as monosaccharides such as glucose and fructose and disaccharides such as maltose and sucrose, dextrin, and cyclodextrin, and synthetic sweeteners such as saccharin and aspartame. The amount of the natural carbohydrates may be in the range of about 0.01 to 10 g, for example, 0.01 to 0.1 g, based on 100 ml of the composition.

The composition according to the present invention may further include diverse nutrients, vitamins, minerals, flavoring agents, colorants, pectic acid and salts thereof, alginic acid and salts thereof, organic acid, protective colloid thickening agents, pH controllers, stabilizers, preservatives, glycerin, alcohol, carbonating agents used in carbonated beverages. The composition according to the present invention may further include fruit flesh for preparing natural fruit juices, fruit juice beverages, and vegetable beverages. These ingredients may be used independently or in combinations. The amount of the additional ingredients may be in the range of 0.01 to 0.1 parts by weight based on 100 parts by weight of the composition according to the present invention.

According to another embodiment of the present invention, a method of preventing or treating erectile dysfunction of an individual includes administrating a pharmaceutical composition for preventing or treating erectile dysfunction into an individual, the pharmaceutical composition including angiopoietin-4 protein or an angiopoietin-4 protein-encoding polynucleotide as an active ingredient in an effective amount to treat erectile dysfunction.

The pharmaceutical composition for preventing or treating erectile dysfunction is the same as described above.

The term "individual" used in regard to the method described above refers to a subject in need of the treatment of diseases. The individual may be a subject that has erectile dysfunction symptoms or is likely to represent erectile dysfunction symptoms. The individual may be mammals, for example, at least one selected from the group consisting of human or non-human primates, mice, rats, dogs, cats, horses, and cattle.

The term "effective amount to treat erectile dysfunction" used in regard to the method described above refers to an amount in case of which the pharmaceutical composition is administrated into an individual for the improvement of erection, e.g., increase in erectility and/or erection duration time, compared to the case of which the pharmaceutical composition is not administrated into an individual. The "effective amount to treat erectile dysfunction" may be determined according to factors such as type and severity of disease, age and sex of a patient, sensitivity to drugs, time of administration, route of administration, excretion rate, treatment period, and drugs used at the same time, and other factors well known in the medical field. That is, a desirable effective amount to achieve a maximum of efficiency without side effects may be easily chosen by those skilled in the art in consideration of all the above factors. The effective amount used herein may be in the range of 0.00001 mg/kg to 1000 mg/kg, for example, 0.00001 mg/kg to 100 mg/kg, 0.00001 mg/kg to 10 mg/kg, 0.00001 mg/kg to 10 mg/kg, 0.0001 mg/kg to 1000 mg/kg, 0.001 mg/kg to 1000 mg/kg, 0.01 mg/kg to 1000 mg/kg, 0.1 mg/kg to 1000 mg/kg, 1 mg/kg to 1000 mg/kg, 10 mg/kg to 1000 mg/kg, or 100 mg/kg to 1000 mg/kg.

Here, any route of administration that may deliver the pharmaceutical composition to reach erectile tissue of the penis may be used. Examples of the route of administration include oral administration, rectal administration, and intravenous, intramuscular, subcutaneous, and intracavernous administration.

The pharmaceutical composition may increase the intracavernous pressure. The pharmaceutical composition may increase an endothelial cell-specific protein level in endothelial cells, and examples of the endothelial cell-specific protein include PECAM-1, p-eNOS, and a combination thereof.

The erectile dysfunction may be caused by damage to penile endothelial cells, and the damage to the penile endothelial cells may be caused by at least one cause selected from the group consisting of hyperlipidemia, diabetes, hypertension, and damage to penis nerves.

The composition according to the present invention may be used for the prevention or treatment of erectile dysfunction alone or in combination with surgery, radiation therapy, hormone therapy, chemotherapy, and methods using a biological response modifier.

Hereinafter, one or more embodiments of the present invention will be described in detail with reference to the following examples, experimental examples, and preparation examples. However, these examples, experimental examples, and preparation examples are not intended to limit the purpose and scope of the one or more embodiments of the present invention.

EXAMPLE 1

Expression of Angiopoietin-4 Protein 1-1. Expression of Angiopoietin-4 Protein in HUVEC and Penile Fibroblast Cell In order to identify expression of angiopoietin-4 protein in human umbilical vein endothelial cells (HUVECs) and penile fibroblast cells, the HUVECs and penile fibroblast cells were respectively subjected to immunoprecipitation.

In more detail, HUVECs and fibroblast cells isolated from the penis and subjected to a primary incubation were used. HUVECs were cultivated in a 0.2% gelatin-coated cell culture dish using an M-199 culture medium supplemented with nutrients, a growth factor, and antibiotics, and fibroblast cells were cultivated in a Dulbecco's Modified Eagle Medium (DMEM) supplemented with nutrients and antibiotics. Each of the cells was cultivated in an incubator at 37° C. in 5% $CO_2$ and humid condition.

The cultivated HUVECs and penile fibroblast cells were respectively subjected to immunoprecipitation. Immunoprecipitation was performed as follows.

HUVECs and penile fibroblast cells were respectively cultivated in 100 mm culture dishes. The dishes were washed three times with phosphate buffered saline (PBS), and the cells were lysed using a radioimmunoprecipitation assay buffer (RIPA buffer) to extract proteins from the cells. Proteins obtained from each of the cells were quantified to prepare samples having the same amount of 500 mg. Then, 1 mg of angiopoietin-4 protein antibody was added to each of the samples, and the reaction mixtures were maintained for 8 hours. Anti-IgG antibody was added to 500 mg of the extracted proteins to prepare an IgG control group, and the IgG control group was subjected to the same reaction as the aforementioned experimental group. Then, 50 mL of protein G agarose beads were added to each of the experimental groups, and the reaction mixtures were maintained at 4° C. overnight. The reaction mixture was centrifuged at 13,000 rpm for 10 minutes, and a supernatant was removed, followed by washing three times with PBS. Then, a supernatant was removed therefrom and an SDS loading dye was added thereto. Then, the resultant was heat-treated at 100° C. to separate the proteins from the beads. A supernatant including the separated proteins was subjected to a western blot assay. The western blot assay was performed by separating proteins through SDS-polyacrylamide gel electrophoresis and transferring the electrophoresed proteins to a nitrocellulose membrane using anti-angiopoietin-4 protein antibody, thereby examining the degree of expression of angiopoietin-4 protein.

Figure 1:
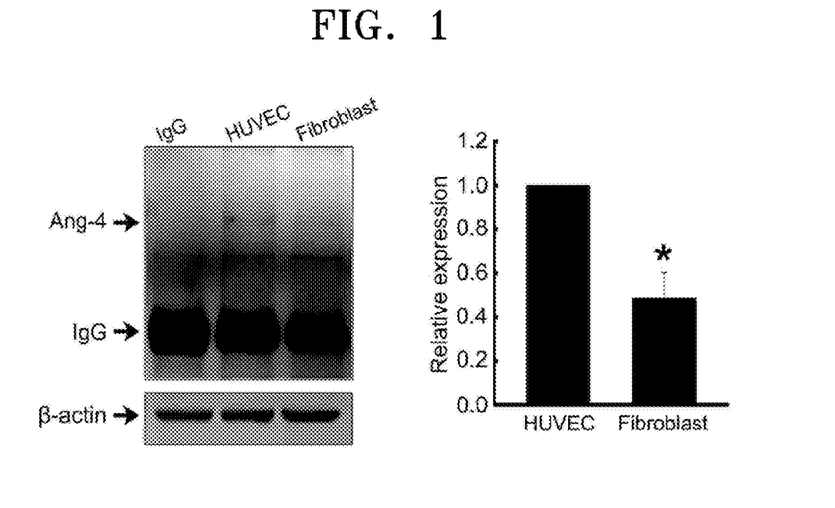
FIG. 1 illustrates immunoprecipitation-western blot assay results exhibiting expression levels of angiopoietin-4 protein of human umbilical vein endothelial cells (HUVECs) and penile fibroblast cells.

The results are illustrated in FIG. 1.

As a result of the immunoprecipitation-western blot assay of the HUVECs and penile fibroblast cells as illustrated in FIG. 1, it was confirmed that angiopoietin-4 protein was more expressed in HUVECs, which are vascular endothelial cells, than the fibroblast cells.

1-2. Expression of Angiopoietin-4 Protein in Penile Vascular Endothelial Cell

In order to identify expression of angiopoietin-4 protein in penile vascular endothelial cells, platelet/endothelial cell adhesion molecule-1 (PECAM-1) and angiopoietin-4 protein were subjected to immunohistochemical staining in a corpus cavernosum tissue of a normal mouse, followed by confocal microscopy.

In more detail, penile tissue was fixed at 4° C. in a 4% p-formaldehyde for 24 hours, and sliced to a thickness of 7 µm using a cryostat to prepare penile tissue samples. Then, a prepared penile tissue sample was placed on a slide and fixed in a 4% p-formaldehyde for about 5 minutes. The fixed penile tissue sample was washed three times using a washing buffer solution (2% FBS+0.1% sodium azide in PBS) and blocked for 1 hour using a non-specific protein blocking buffer solution (5% BSA in PBS). The sample was reacted with a first antibody (anti-PECAM-1 hamster antibody and anti-angiopoietin-4 protein goat antibody) at a ratio of 1:100 at 4° C. overnight, and then the reaction mixture was washed three times using a washing buffer solution to remove the remaining antibodies. Then, the resultant was reacted with a second antibody (FITC-labeled anti-hamster antibody or TRITC-labeled anti-goat antibody), which was prepared to identify antibodies specifically reacted with PECAM-1 and angiopoietin-4 protein in a fluorescent method, at a ratio of 1:1000 at room temperature for 2 hours. After the reaction was terminated, the remaining antibodies were removed by washing the reaction mixture three times using the washing buffer solution, followed by analyzing the degree of expression using a fluorescence microscope or a confocal microscope capable of identifying a fluorescent substance. The results are illustrated in FIG. 2.

Figure 2:
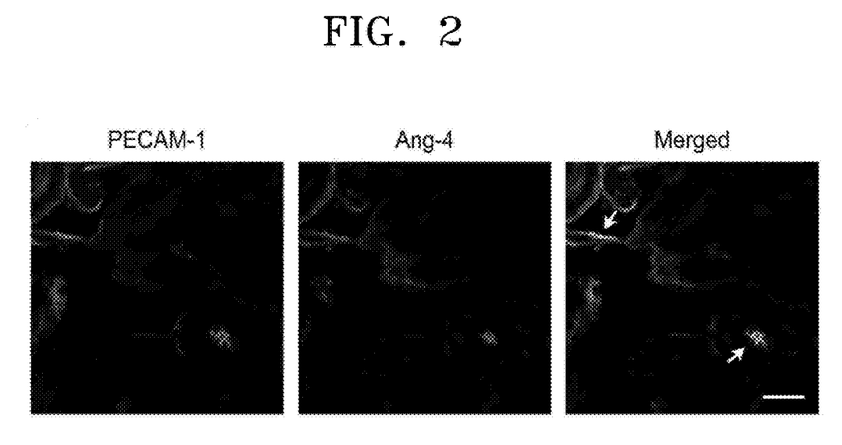
FIG. 2 illustrates expression levels of angiopoietin-4 protein in penile sinusoidal and vascular endothelial cells analyzed using a confocal microscope.

As a result of the analysis using the confocal microscope as illustrated in FIG. 2, expression of angiopoietin-4 protein was mainly observed in vascular endothelial cells in normal penile tissue, particularly, in artery of corpus cavernosum.

1-3. Expression of Angiopoietin-4 Protein in Penis of Diabetic Mouse Model

In order to analyze the degree of expression of angiopoietin-4 protein in the penis of a diabetic mouse model, diabetes was induced in mice, and expressions of angiopoietin-4 protein gene and protein in penile tissue of 8-week-old diabetic mice were compared with those of normal mice through a cDNA microarray and a western blot assay.

In more detail, 2-month-old male mice (C57BL/6J) were used to prepare a diabetic mouse model. Streptozotocin was administered into mice in a concentration of 50 mg/kg via an intraperitoneal injection for 5 consecutive days to induce diabetes. At 8 weeks from the inducing of diabetes, diabetes was confirmed by checking blood glucose levels and weights of the mice, and penile tissue was collected to perform experiments. Expression of angiopoietin-4 protein in penile tissue of diabetic mice was compared with that in normal mice using a cDNA microarray and a western blot assay.

1-3-1. CDNA Microarray

A cDNA microarray was performed in corpus cavernosum tissue after removing urethra and dosal vascular nerve segments from penile tissue. The tissue was crushed and treated with trizol to extract RNA, and the resultant was subjected to a cDNA microarray analysis. The results are illustrated in FIG. 3.

Figure 3:
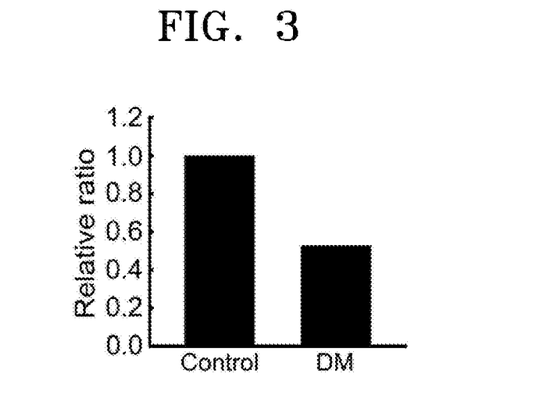
FIG. 3 is a graph illustrating expression levels of angiopoietin-4 protein in penile tissue of a diabetic mouse model analyzed using a cDNA microarray.

As a result of the cDNA microarray analysis as illustrated in FIG. 3, it was confirmed that gene expression of angiopoietin-4 protein was reduced in the penis of the diabetic mice when compared with the normal mice.

1-3-2. Western Blot Assay

A cDNA microarray was performed in corpus cavernosum tissue of normal mice and diabetic mice after removing urethra and dorsal vascular nerve segments from penile tissue, followed by a western blot assay in the same manner as in Example 1-2. The results are shown in FIG. 4.

Figure 4:
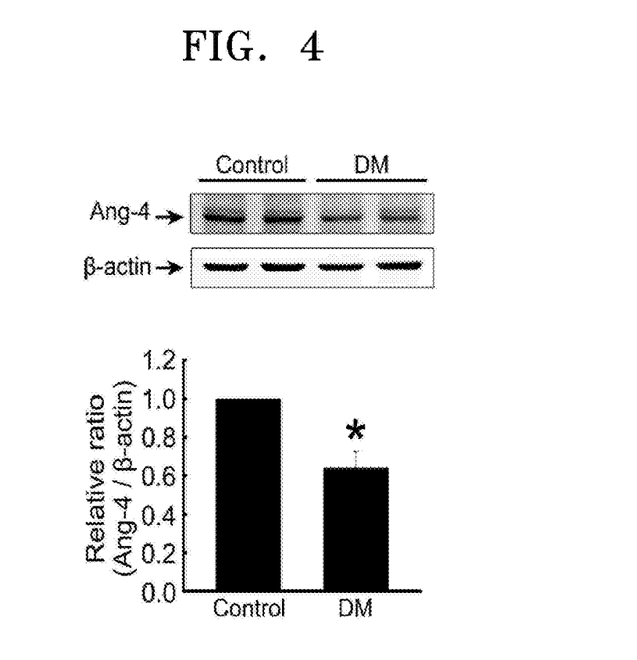
FIG. 4 illustrates expression levels of angiopoietin-4 protein in penile tissue of a diabetic mouse model analyzed using a western blot assay.

As illustrated in FIG. 4, similarly to the cDNA microarray results, it was confirmed that expression of angiopoietin-4 protein was reduced in the penile tissue of the diabetic mice when compared with the normal mice.

EXAMPLE 2

Therapeutic Effect of Angiopoietin-4 protein on Erectile Dysfunction in Diabetic Erectile Dysfunction Mouse Model In order to identify therapeutic effect of angiopoietin-4 protein on erectile dysfunction in a diabetic erectile dysfunction mouse model, 2-month-old male mice (C57BL/6J) were used. The mice were divided into 4 groups, and experiments were conducted (N=10/group; Group 1: normal mice; Group 2: diabetic mice+PBS [20 µl]; Group 3: diabetic mice+angiopoietin-4 protein injection (once) [day 0; 5.8 µg/20 µl]; and Group 4: diabetic mice+angiopoietin-4 protein injection (twice) [day −3, 0; 5.8 µg/20 µl]).

2-1. Analysis of Erectility According to Electrical Stimulation

Angiopoietin-4 protein was administered to the diabetic erectile dysfunction mouse model via intracavernous injection. At 1 week from the intracavernous injection, erectility was measured by stimulating corpus cavernosum nerves.

Erectility was measured using a method including making an incision in the lower left side section of the abdomen of a prepared mouse, and opening the incision such that corpus cavernosum nerves (penile nerves) located in an external dorsal portion of prostate gland is visible. A platinum electrode was located at the penile nerves for electrical stimulation, and then an electrical stimulation (1 to 5 V, 12 Hz) was applied thereto for about 1 minute for erection. In this case, the intracavernous pressure was measured using a catheter inserted into the corpus cavernosum through a pressure transmitter (BioSpec® systems, U.S.A.) connected to a computer for collection of data regarding the intracavernous pressure while erection is maintained, and the measured pressure indicates erectility of the penis.

Figure 5:
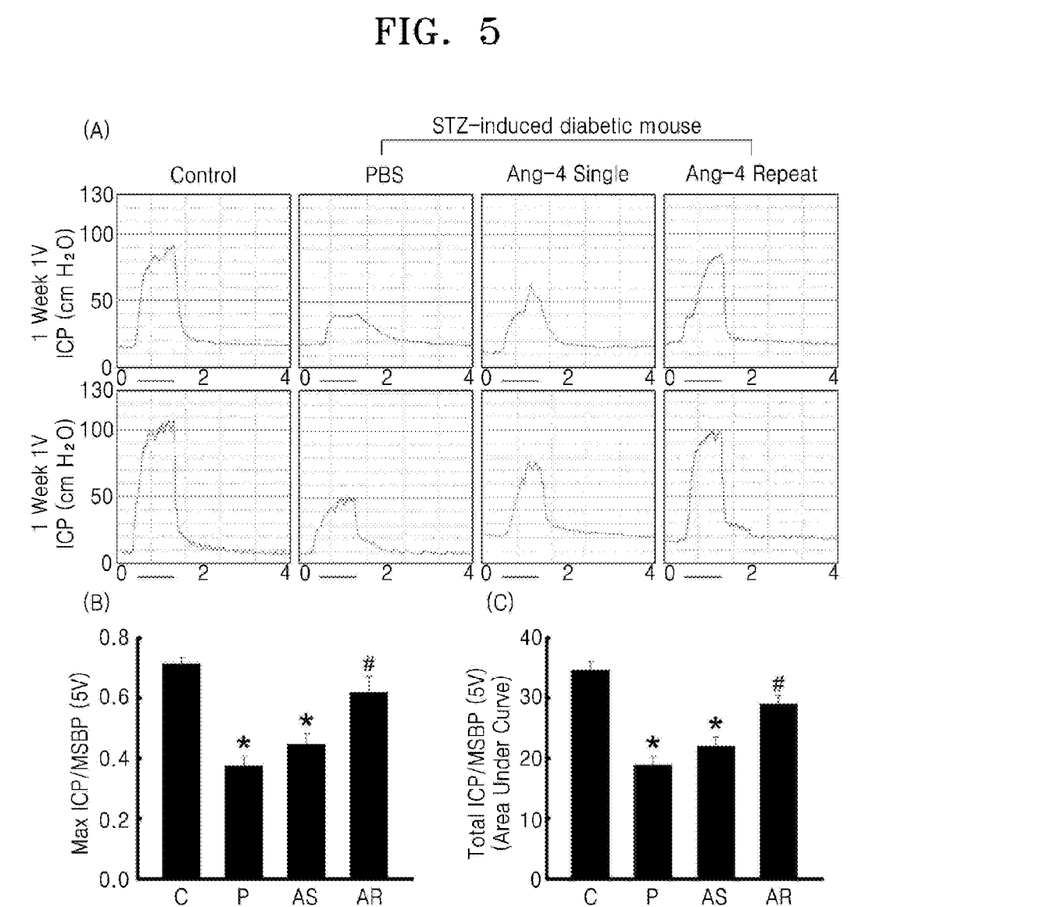
FIGS. 5A to 5C illustrates intracavernous pressure (erectile function) of a diabetic mouse model after electrical stimulation on penile nerves, with respect to administration of angiopoietin-4 protein (C: Control, P: PBS, AS: Ang-4 Single, AR: Ang-4 Repeat)

FIGS. 5A to 5C illustrate intracavernous pressures (erectilities) according to electrical stimulation on the penile nerves of the angiopoietin-4 protein-treated group and the control group of the diabetic mouse model.

FIG. 5A illustrates erectilities of corpus cavernosum of mice treated with angiopoietin-4 protein once or twice, and then treated with electrical stimulation of 1V or 5V at 1 week from the angiopoietin-4 protein administration. The intracavernous pressure (ICP) of the Y-axis of FIG. 5A that is defined as a pressure inside the penis during erection is an index indicating erectility. The X-axis of FIG. 5A indicates time after electrical stimulation, and the electrical stimulation performed for 1 minute was indicated as a black bar in the X-axis.

In addition, FIG. 5B illustrates erectility obtained by dividing a maximal intracavernous pressure by a mean systolic blood pressure (MSBP). FIG. 5C also illustrates erectility obtained by dividing an area under the intracavernous pressure curve (Total ICP) by a MSBP. This is because blood pressure may affect the intracavernous pressure.

As illustrated in FIGS. 5A to 5C, the group treated with angiopoietin-4 protein twice Ang-4 Repeat exhibited the highest improvement in erectility compared to the PBS-treated group, and the erectility was increased up to about 87% of the normal control group. It was confirmed that two parameters related to erection of the penis, i.e., maximal intracavernous pressure and area of the intracavernous pressure curve, are significantly increased after the administration of angiopoietin-4 protein.

2-2. Expression of PECAM-1 and p-eNOS as Penile Vascular Endothelial Cell-Specific Protein The penis consists of unique vascular tissue, and normal activity of penile blood vessel is required to obtain normal erection. Particularly, endothelial nitric oxide synthase (eNOS) generated in penile vascular endothelial cells is an enzyme mainly generating nitric oxide (NO) that plays an important role in relaxation of the penile blood vessel and erection of the penis thereby.

Abnormal structure or abnormal activity of the penile blood vessel may cause reduction in erectility. Thus, a structural change of penile erectile tissue was measured in diabetic mice in which diabetes was induced by administrating streptozotocin into normal mice. Expression of PECAM-1 and activation of phosphorylated endothelial nitric oxide synthase (p-eNOS), i.e., the degree of phosphorylation, in corpus cavernosum tissue in a diabetic erectile dysfunction mouse model were measured via immunohistochemical staining, followed by confocal microscopy. A quantitative change of vascular endothelial cells and activation of eNOS were evaluated.

Penile tissue was fixed at 4° C. in a 4% p-formaldehyde for 24 hours, and sliced to a thickness of 7 μm using a cryostat to prepare penile tissue samples. A prepared corpus cavernosum tissue sample was placed on a slide and fixed in a 4% p-formaldehyde for about 5 minutes for analysis of expressions of PECAM-1 and p-eNOS. The fixed penile tissue sample was washed three times using a washing buffer solution (2% FBS+0.1% sodium azide in PBS) and blocked for 1 hour using a non-specific protein blocking buffer solution including (5% BSA in PBS). The sample was reacted with a first antibody (anti-PECAM-1 hamster antibody, and anti-p-eNOS goat antibody) at a ratio of 1:100 at 4° C. for 16 hours, and then the reaction mixture was washed three times using the washing buffer solution to remove the remaining antibodies. Then, the resultant was reacted with a second antibody (FITC-labeled anti-goat antibody or TRITC-labeled anti-hamster antibody), which was prepared to identify antibodies specifically reacted with PECAM-1 and p-eNOS in a fluorescent method, at a ratio of 1:1000 at room temperature for 2 hours. After the reaction was terminated, the remaining antibodies were removed by washing the sample three times using the washing buffer solution, followed by analyzing the degree of expression using a fluorescence microscope or a confocal microscope capable of identifying a fluorescent substance.

Figure 6:
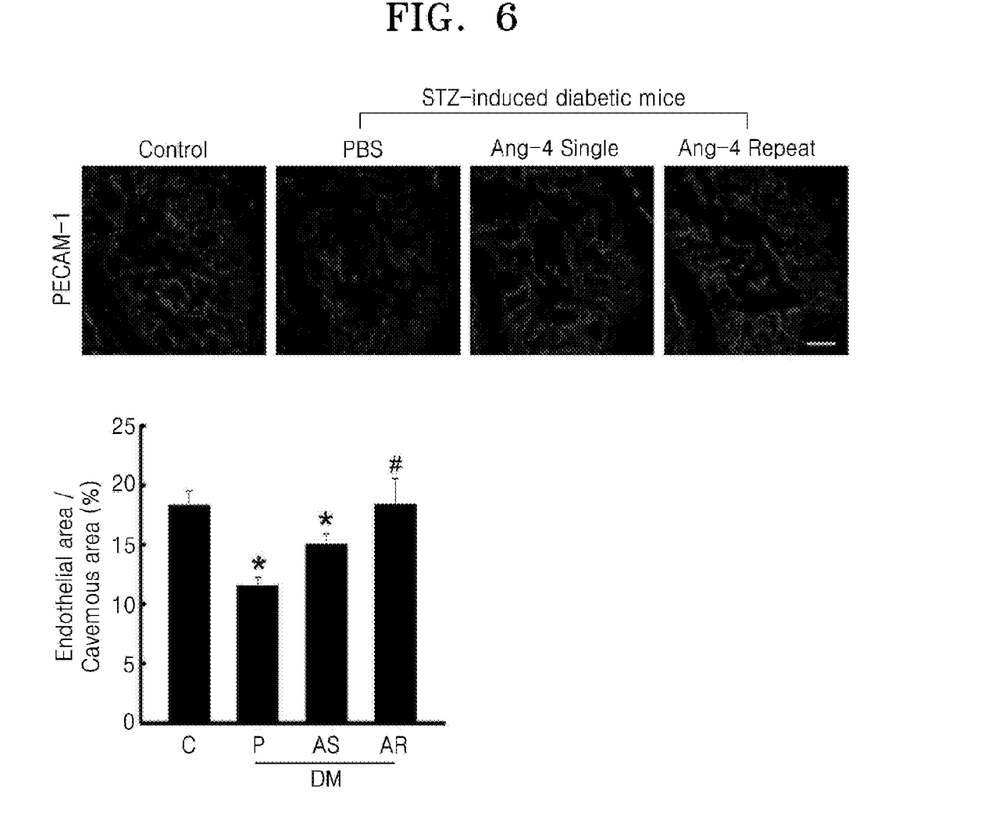
FIG. 6 illustrates expression levels of platelet/endothelial cell adhesion molecule-1 (PECAM-1), which is a vascular endothelial cell-specific protein, in corpus cavernosum tissue of a diabetic mouse model analyzed using a confocal microscope, with respect to administration of angiopoietin-4 protein (C: Control, P: PBS, AS: Ang-4 Single, AR: Ang-4 Repeat)

FIG. 6 illustrates expressions of PECAM-1 that is vascular endothelial cell-specific protein, in corpus cavernosum tissue of diabetic mice treated with angiopoietin-4 protein and the control group. Expressions of PECAM-1 and p-eNOS are illustrated in FIG. 7.

As a result of analysis of expression of PECAM-1, as vascular endothelial cell-specific protein, using the confocal microscope in the corpus cavernosum tissue of diabetic mice treated with angiopoietin-4 protein and the control group as illustrated in FIG. 6, it was confirmed that the number of vascular endothelial cells was considerably reduced in the corpus cavernosum tissue of the PBS-treated diabetic mice group compared with the normal mice. Expression of the vascular endothelial cell-specific protein was increased in the Ang-4 Repeat group into which angiopoietin-4 protein was administered twice compared to the PBS-treated group into which PBS was administered instead of angiopoietin-4 protein and the Ang-4 Single group into which angiopoietin-4 protein was administered once. These results indicate that regeneration of the vascular endothelial cells that was reduced due to diabetes was induced by angiopoietin-4 protein, thereby restoring erectility.

Figure 7:
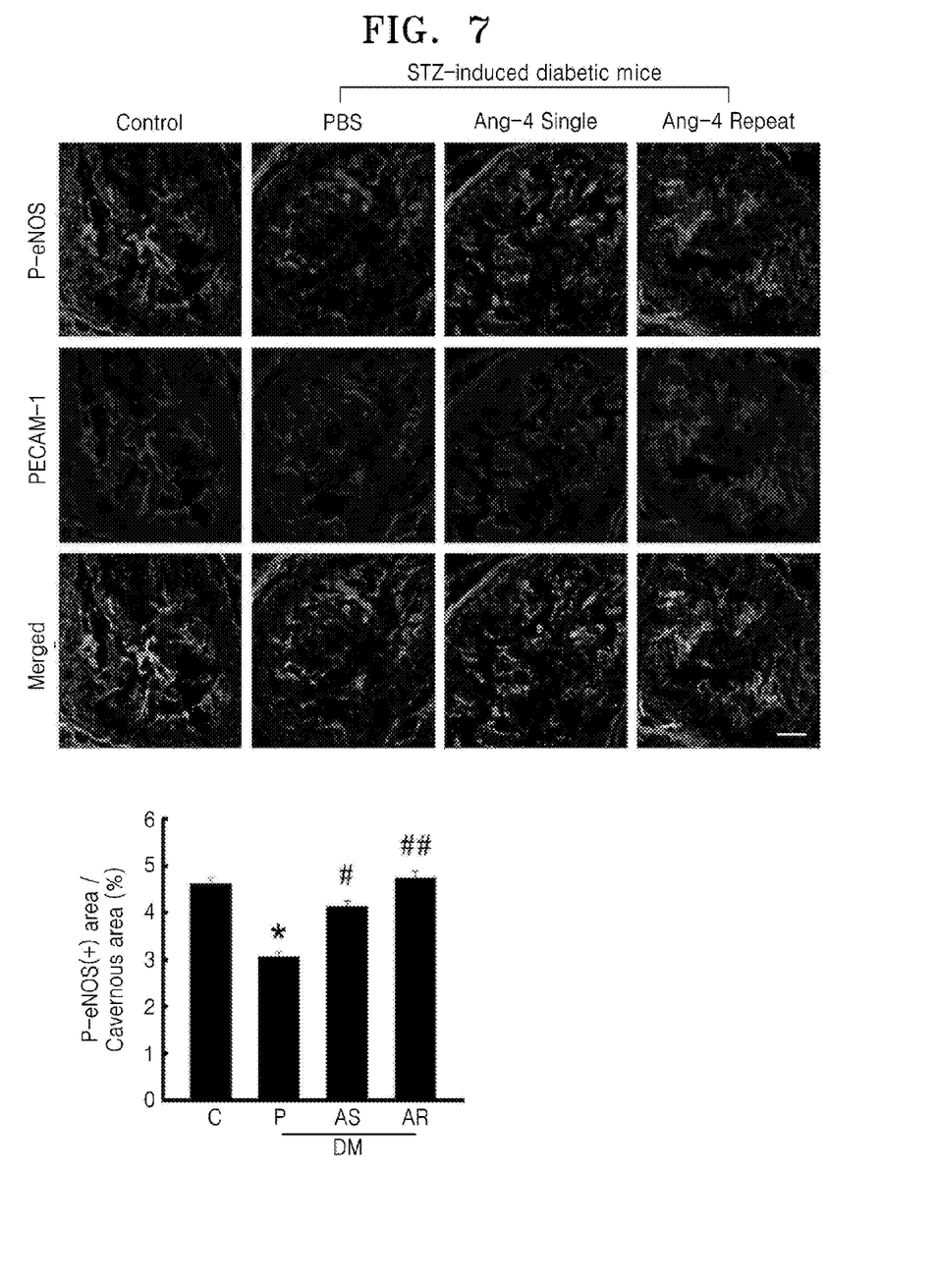
FIG. 7 illustrates expression levels of PECAM-1 and phosphorylated endothelial nitric oxide synthase (p-eNOS), which is a vascular endothelial cell-specific protein, in corpus cavernosum tissue of a diabetic mouse model analyzed using a confocal microscope, with respect to administration of angiopoietin-4 protein (C: Control, P: PBS, AS: Ang-4 Single, AR: Ang-4 Repeat)

As a result of analysis of expressions of PECAM-1 and p-eNOS in penile tissue of the diabetic mice treated with angiopoietin-4 protein and the control group using the confocal microscope as illustrated in FIG. 7, it was confirmed that expression of p-eNOS was considerably reduced in the PBS-treated diabetic mice compared to the normal mice (control group). Expression of p-eNOS was increased in the Ang-4 Repeat group into which angiopoietin-4 protein was administered twice compared to the PBS-treated group into which PBS was administered instead of angiopoietin-4 protein and the Ang-4 Single group into which angiopoietin-4 protein was administered once. These results indicate that activity of p-eNOS that was reduced due to diabetes was increased by angiopoietin-4 protein, thereby restoring erectility.

2-3. Generation of Superoxide Anion in Vascular Endothelial Cell

Diabetes were induced in mice by administering streptozotocin into normal mice, and then generation of superoxide anions were measured in vascular endothelial cells in penile erectile tissue in a diabetic erectile dysfunction mouse model via hydroethidine staining.

Hydroethidine that is an indicator sensitive to redox reaction is used to detect superoxide anion, one of oxygen free radicals in cells. Reaction between superoxide and hydroethidine produces ethidium, as a two-electron oxidized product. Ethidium absorbs a wavelength of 500 to 530 nm when attached to DNA and emits fluorescence at 590 to 620 nm. Superoxide anion is an anionic free radial with strong reactivity. NADPH oxidase generates a large amount of superoxide anions which are harmful and may cause damage to DNA.

The samples were subjected to immunofluorescence with anti-PECAM-1 antibody and washed in the same manner as in Example 2-2, and treated with hydroethidine (1 mM in PBS) for 30 minutes to analyze the degree of expression using a fluorescence microscope or a confocal microscope capable of identifying a fluorescent substance.

Figure 8:
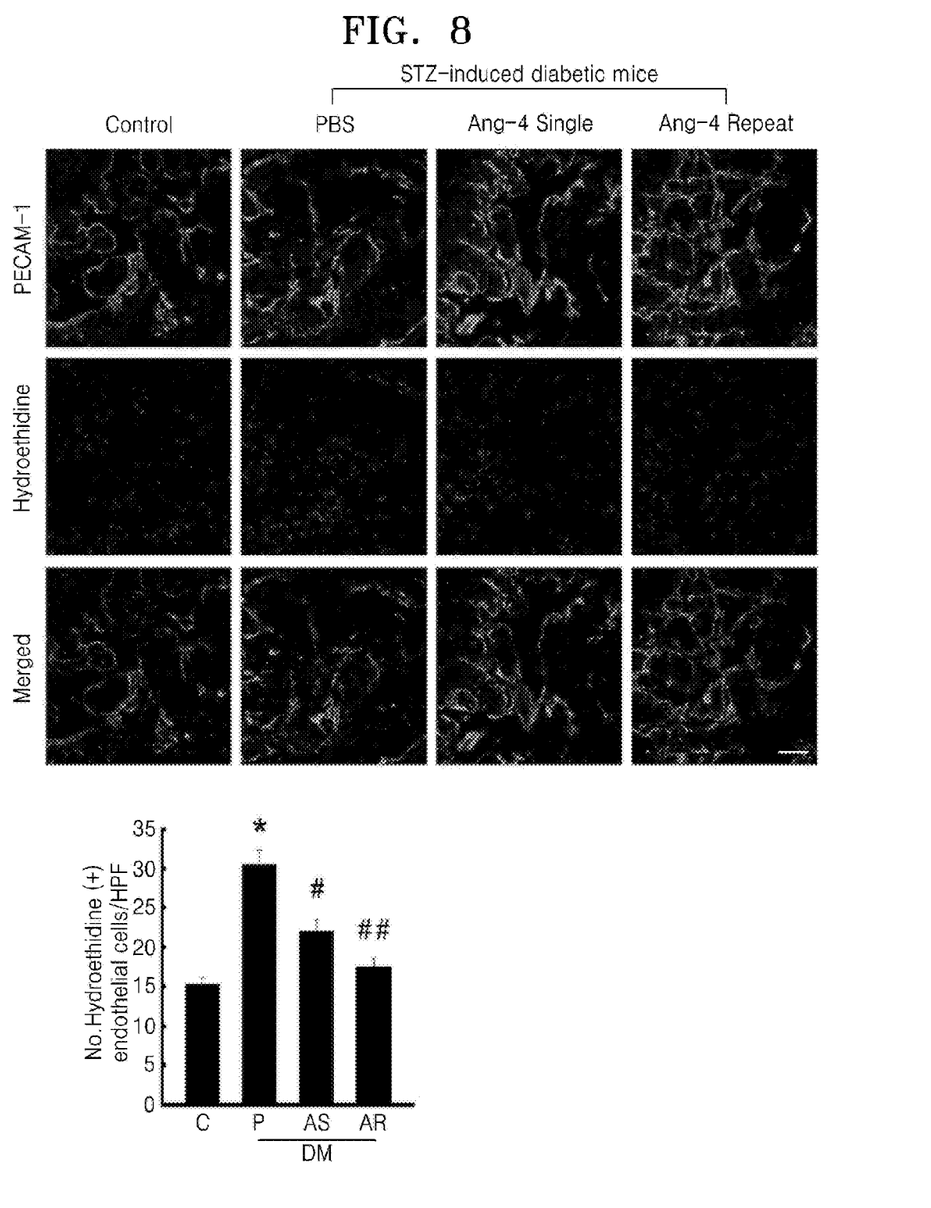
FIG. 8 illustrates expression levels of superoxide anions in vascular endothelial cells of a diabetic mouse model analyzed using fluorescence staining with hydroethidine and a confocal microscope, with respect to administration of angiopoietin-4 protein (C: Control, P: PBS, AS: Ang-4 Single, AR: Ang-4 Repeat)

FIG. 8 illustrates the degree of fluorescence in penile tissue of the diabetic mice treated with aniopoietin-4 protein and the control group after treatment of hydroethidine that reacts with superoxide anions using a confocal microscope.

As illustrated in FIG. 8, it was confirmed that superoxide anions are considerably increased in the penis of the diabetic mice treated with PBS compared to the normal mice (control). It was confirmed that the generation of superoxide anions was reduced in the Ang-4 Repeat group into which angiopoietin-4 protein was administered twice compared to the PBS-treated group into which PBS was administered instead of angiopoietin-4 protein and the Ang-4 Single group into which angiopoietin-4 protein was administered once. These results indicate that superoxide anions that were increased due to diabetes were reduced by angiopoietin-4 protein, thereby restoring erectility.

EXAMPLE 3

Effect of Angiopoietin-4 Protein in HUVECs

Tyrosine kinase with Ig and EGF homology domains 2 (Tie-2) is an angiopoietin family receptor membrane protein. Tie-2 is expressed in vascular endothelial cells in a large amount and affects angiogenesis. Angiopoietin-1 and angiopoietin-2 are main ligands. Angiopoietin-1 regulates survival, migration, and proliferation of vascular endothelial cells by phosphorylating Tie-2, and angiopoietin-2 plays opposite roles of angiopoietin-1. Effect of angiopoietin-4 protein on phosphorylation of a Tie-2-AKT-eNOS system, which is one of the routes involved in the survival, migration, and proliferation of vascular endothelial cells was evaluated through a western blot assay.

Samples were divided into a control group and an angiopoietin-4 protein-treated group. HUVECs were treated with 200 ng/ml of angiopoietin-4 protein and subjected to the western blot assay.

Figure 9:
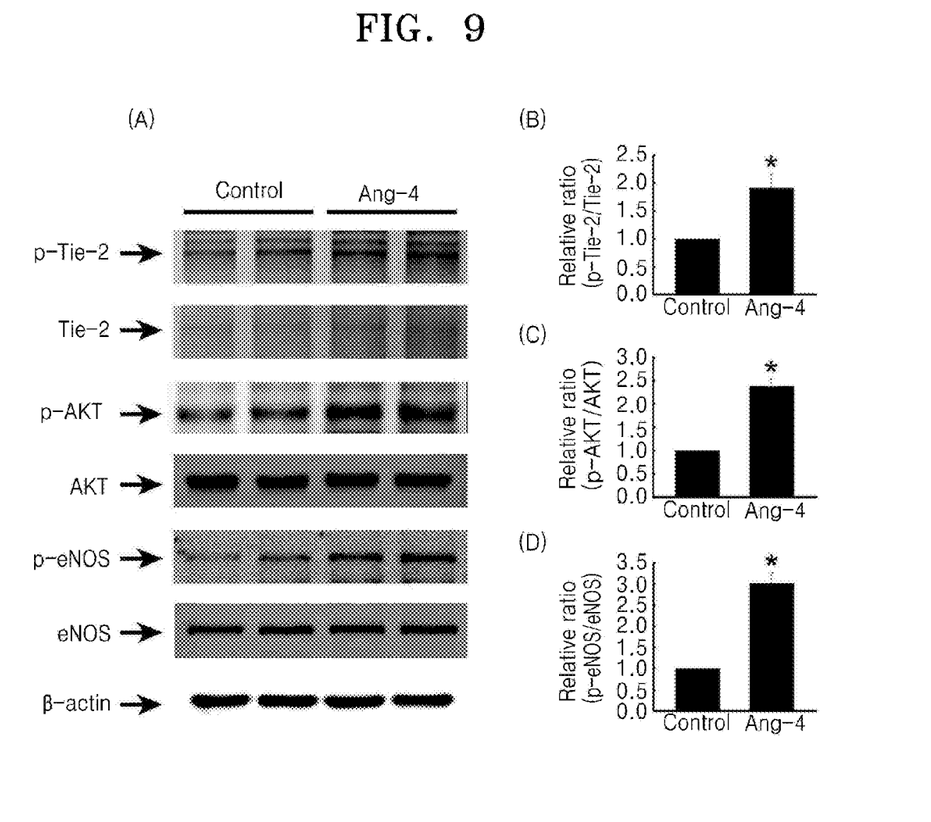
FIG. 9 illustrates phosphorylation results of Tie-2, Akt, and eNOS in umbilical vein endothelial cell analyzed using a western blot assay, with respect to administration of angiopoietin-4 protein.

The results are shown in FIG. 9, i.e., (A) to (D) of FIG. 9.

As results of the western blot assay as illustrated in FIG. 9, phosphorylation of Tie-2 was increased in the angiopoietin-4 protein-treated HUVECs when compared to the control group. It was also confirmed that larger amounts of AKT and eNOS, which are sub signals thereof, were phosphorylated when compared to the control group ((A) of FIG. 9). In addition, as a result of quantitatively analyzing amounts of phosphorylated pTie-2/Tie2 ((B) of FIG. 9), pAKT-AKT ((C) of FIG. 9), and p-eNOS/eNOS ((D) of FIG. 9), phosphorylation was increased mostly in the angiopoietin-4 protein-treated groups by 1.9 times (Tie-2), 2.4 times (AKT), and 3.0 times (eNOS) when compared to the control group. These results indicate that angiopoietin-4 protein affects survival, migration, and proliferation of the vascular endothelial cells.

Based on the results of these experiments, angiopoietin-4 protein according to the present invention may increase intracavernous pressure by inducing regeneration of vascular endothelial cells, which was reduced due to diabetes, increasing expressions of vascular endothelial cell-specific PECAM-1 and p-eNOS, and increasing phosphorylation of Tie-2 in vascular endothelial cells, thereby affecting the survival, migration, and proliferation of the vascular endothelial cells. Thus, angiopoietin-4 protein has an effect on erectile dysfunction to improve erectility, and thus may be efficiently applied to prevention or treatment of erectile dysfunction.

Hereinafter, preparation examples of pharmaceutical compositions and functional foods including the composition according to the present invention will be described. However, these preparation examples are not intended to limit the scope of the present invention.

Preparation Example 1

Preparation of Pharmaceutical Composition 1-1. Preparation of Powder

| | |
|---|---|
| Angiopoietin-4 protein | 20 mg |
| Lactose | 100 mg |
| Talc | 10 mg |

Powder was prepared using a known method by mixing the ingredients above and filling the mixture in an airtight pack.

1-2. Preparation of Tablet

| | |
|---|---|
| Angiopoietin-4 protein | 10 mg |
| Corn starch | 100 mg |
| Lactose | 100 mg |
| Magnesium stearate | 2 mg |

Tablet was prepared using a known method by mixing the ingredients above.

1-3. Preparation of Capsule

| | |
|---|---|
| Angiopoietin-4 protein | 10 mg |
| Crystalline cellulose | 3 mg |
| Lactose | 14.8 mg |
| Magnesium stearate | 0.2 mg |

Capsule was prepared using a known method by mixing the ingredients above and filling the mixture in a gelatin capsule.

1-4. Preparation of Injection Solution

| | |
|---|---|
| Angiopoietin-4 protein | 10 mg |
| Mannitol | 180 mg |
| Sterilized distilled water for injection | 2974 mg |
| $Na_2HPO_4 \cdot H_2O$ | 26 mg |

Injection solution was prepared using a known method by filling the ingredients above in a 2 ml ample.

1-5. Preparation of Liquid

| | |
|---|---|
| Angiopoietin-4 protein | 20 mg |
| High fructose corn syrup | 10 g |
| Mannitol | 5 g |
| Purified water | appropriate amount |

Liquid was prepared using a known method by dissolving the ingredients above in purified water, adding an appropriate amount of lemon flavor thereto, mixing the ingredients, and adjusting the total volume to be 100 mL by adding purified water thereto, filling the resultant in a brown bottle, and sterilizing the resultant.

Preparation Example 2

Preparation of Food Composition 2-1. Preparation of Functional Food

| | |
|---|---|
| Angiopoietin-4 protein | 100 mg |
| Vitamin mixture | appropriate amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin BC | 10 mg |
| Biotin | 10 μg |
| Nicotinic acid amide | 1.7 mg |
| Folic acid | 50 μg |
| Calcium pantothenate | 0.5 mg |
| Mineral mixture | appropriate amount |
| Ferrous sulfate | 1.75 mg |
| Zinc oxide | 0.82 mg |
| Magnesium carbonate | 25.3 mg |
| Potassium phosphate, monobasic | 15 mg |
| Potassium phosphate, dibasic | 55 mg |
| Potassium citrate | 90 mg |
| Calcium carbonate | 100 mg |
| Magnesium chloride | 24.8 mg |

Although the composition ratio between vitamins and minerals was determined by mixing vitamins and minerals suitable for functional foods according to an exemplary embodiment, it may vary. According to a known method for preparing functional foods, the ingredients above were mixed to prepare granules. Then, the granules may be used in the preparation of functional food composition.

2-2. Preparation of Functional Beverage

| | |
|---|---|
| Angiopoietin-4 protein | 100 mg |
| Vitamin C | 15 g |
| Vitamin E (powder) | 100 g |
| Ferrous lactate | 19.75 g |
| Zinc oxide | 3.5 g |
| Nicotinic acid amide | 3.5 g |
| Vitamin A | 0.2 g |
| Vitamin B1 | 0.25 g |
| Vitamin B2 | 0.3 g |
| Water | appropriate amount |

According to a known method for preparing functional beverage, the ingredients above were mixed, stirred at 85° C. for about 1 hour while heating, filtered and contained in a sterile container, and sterilized. The resultant was stored in a refrigerator and used for the preparation of functional beverage composition.

Although the composition ratio of the ingredients was determined by mixing ingredient suitable for favorite drinks according to an exemplary embodiment, it may vary according to class or country of consumers, purpose of use, regional and national tastes.

As described above, according to the one or more of the above embodiments of the present invention, angiopoietin-4 protein increases an endothelial cell-specific protein level to induce regeneration of penile vascular endothelial cells, thereby increasing intracavernous pressure. Thus, angiopoietin-4 protein may be efficiently applied to prevention or treatment of erectile dysfunction.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of treating erectile dysfunction of an individual, the method comprising:
   administrating a pharmaceutical composition for treating erectile dysfunction into an individual, wherein the pharmaceutical composition comprises angiopoietin-4 protein as an active ingredient, wherein the amino-terminal portion of angiopoietin-4 protein is not linked to a polypeptide.

2. The method of claim 1, wherein the pharmaceutical composition may be administered via oral administration, rectal administration, or intravenous, intramuscular, subcutaneous, or intracavernous administration.

3. The method of claim 1, wherein the erectile dysfunction is caused by damage to penile endothelial cells.

4. The method of claim 3, wherein the damage to the penile endothelial cells is caused by at least one cause selected from hyperlipidemia, diabetes, hypertension, and damage to penis nerves.

* * * * *